US010166052B2

(12) United States Patent
Dominik et al.

(10) Patent No.: US 10,166,052 B2
(45) Date of Patent: Jan. 1, 2019

(54) BONE PLATE WITH POLYAXIAL LOCKING MECHANISM

(71) Applicant: Stryker European Holdings I, LLC, Kalamazoo, MI (US)

(72) Inventors: Robert Dominik, Grandvaux (CH); Andreas Wiederkehr, Biel/Bienne (CH); Pierre-Luc Sylvestre, Grenchen (CH)

(73) Assignee: Stryker European Holdings I, LLC, Kalamazoo, MI (US)

( * ) Notice: Subject to any disclaimer, the term of this patent is extended or adjusted under 35 U.S.C. 154(b) by 81 days.

(21) Appl. No.: 15/366,377

(22) Filed: Dec. 1, 2016

(65) Prior Publication Data

US 2017/0164987 A1    Jun. 15, 2017

(30) Foreign Application Priority Data

Dec. 10, 2015  (EP) .................................... 15003519

(51) Int. Cl.
*A61B 17/80*    (2006.01)
(52) U.S. Cl.
CPC ...... *A61B 17/8052* (2013.01); *A61B 17/8047* (2013.01); *A61B 17/8057* (2013.01)
(58) Field of Classification Search
CPC . A61B 17/80; A61B 17/8028; A61B 17/8033; A61B 17/8047; A61B 17/8052; A61B 17/8057
See application file for complete search history.

(56) References Cited

U.S. PATENT DOCUMENTS

| 6,786,909 B1* | 9/2004 | Dransfeld | A61B 17/8052 606/280 |
| 8,870,931 B2* | 10/2014 | Dahners | A61B 17/8047 606/289 |
| 9,101,423 B2* | 8/2015 | Hulliger | A61B 17/8057 |

(Continued)

FOREIGN PATENT DOCUMENTS

WO    2015095126 A1    6/2015

OTHER PUBLICATIONS

European Search Report for Application No. EP15003519 dated Jun. 13, 2016.

*Primary Examiner* — Eric S Gibson
(74) *Attorney, Agent, or Firm* — Lerner, David, Littenberg, Krumholz & Mentlik, LLP

(57) ABSTRACT

A bone plate has a first and a second surface opposite to the first surface, and a deformable contact surface region. The plate has a through hole defining a through hole axis and an inner surface of the bone plate and extending from the first surface through the bone plate to the second surface. The contact surface may be formed by at least part of the inner surface, wherein the deformable contact region comprises a plurality of cavities at least partially surrounding the through hole and each extending in a height direction of the bone plate. Alternatively, the deformable contact region may comprise at least one cavity surrounding the through hole in a circumferential direction of the through hole. Also provided is a bone plate system comprising the bone plate and a fastening member being configured to cooperate with the deformable contact region of the bone plate.

23 Claims, 9 Drawing Sheets

(56) References Cited

U.S. PATENT DOCUMENTS

| | | | |
|---|---|---|---|
| 2004/0073218 A1* | 4/2004 | Dahners | A61B 17/8057 606/287 |
| 2006/0116678 A1* | 6/2006 | Impellizzeri | A61B 17/8057 606/291 |
| 2006/0200148 A1* | 9/2006 | Matthys | A61B 17/8057 606/281 |
| 2008/0234677 A1* | 9/2008 | Dahners | A61B 17/8047 606/60 |
| 2009/0048605 A1* | 2/2009 | Yurek | A61B 17/8052 606/104 |
| 2010/0016858 A1* | 1/2010 | Michel | A61B 17/8057 606/70 |
| 2010/0082070 A1* | 4/2010 | Diez | A61B 17/80 606/286 |
| 2011/0015682 A1* | 1/2011 | Lewis | A61B 17/8047 606/305 |
| 2011/0184415 A1 | 7/2011 | Anderson et al. | |
| 2011/0202092 A1 | 8/2011 | Frigg et al. | |
| 2011/0313421 A1* | 12/2011 | Sidebotham | A61B 17/8047 606/70 |
| 2011/0319943 A1* | 12/2011 | Donahoe | A61B 17/7059 606/290 |
| 2012/0143193 A1* | 6/2012 | Hulliger | A61B 17/8052 606/70 |
| 2012/0203285 A1* | 8/2012 | Rotini | A61B 17/8057 606/286 |
| 2013/0184765 A1* | 7/2013 | Beyar | A61B 17/8052 606/281 |
| 2013/0289628 A1 | 10/2013 | Fritzinger | |
| 2014/0066998 A1 | 3/2014 | Martin | |
| 2015/0112355 A1 | 4/2015 | Dahners et al. | |
| 2015/0327897 A1 | 11/2015 | Hulliger | |
| 2017/0164987 A1* | 6/2017 | Dominik | A61B 17/8052 |

* cited by examiner

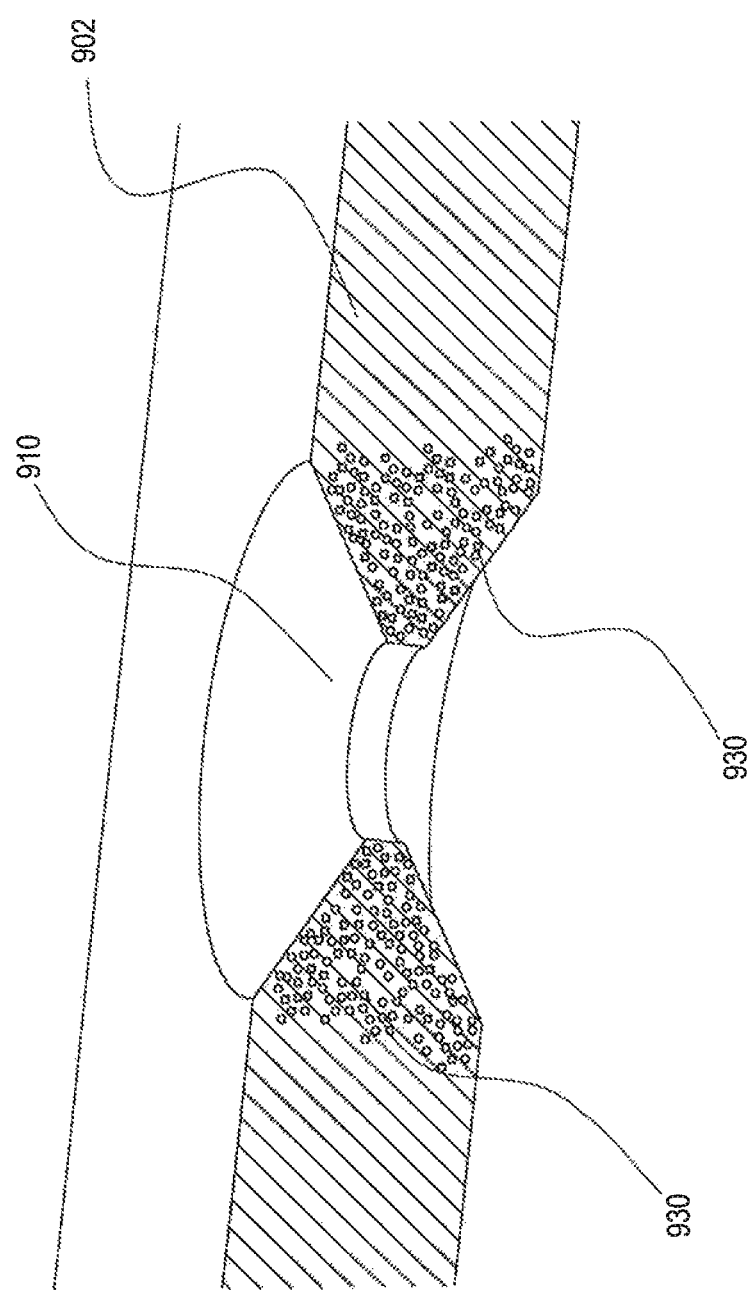

BONE PLATE WITH POLYAXIAL LOCKING MECHANISM

CROSS-REFERENCE TO RELATED APPLICATIONS

This application claims the benefit of the filing date of European Patent Application No. 15003519.4 filed Dec. 10, 2015, the disclosure of which is hereby incorporated herein by reference.

BACKGROUND OF THE INVENTION

The present disclosure generally relates to a bone plate. The disclosure also relates to a bone plate system comprising the bone plate and a fastening member configured to cooperate with the bone plate, in particular for being used in orthopaedic surgical applications.

It is known to use bone plates for treating bone fractures. Specifically, for fixing two or more bone parts of a fractured bone with respect to each other, a bone plate is connected by fastening members such as screws to the two or more bone parts, thereby providing a structural support to the fractured bone and allowing the fractured bone to heal properly.

Due to the variability of the fracture lines and the limited bone volume into which the fastening members can be inserted, it is often important for a surgeon to have the possibility to freely select the insertion angle, i.e., the angle between the bone plate and the fastening member in an inserted state of the fastening member. It is also important that the selected insertion angle relative to the bone plate cannot change in the implanted state of the bone plate system. To this end, a variable angle locking mechanism for locking the bone plate with the fastening members needs to be provided. Such a variable angle locking mechanism is sometimes also called a polyaxial locking mechanism.

In addition, for providing a structural support to the fractured bone without pressing the bone plate onto the fractured bone, it is sometimes necessary that the interface between the bone plate and the fastening member is configured such that it provides a high bending resistance, i.e., a high resistance against deformation when a bending load is acting upon the fastening member.

BRIEF SUMMARY OF THE INVENTION

It is an aspect of the present disclosure to provide a bone plate with a polyaxial locking mechanism which allows a surgeon to freely select the insertion angle of a fastening member and which offers a sufficient stability in a locked state of the polyaxial locking mechanism.

According to a first aspect, a bone plate which comprises a first surface and a second surface opposite to the first surface, a deformable contact region comprising a contact surface, and a through hole defining a through hole axis and an inner surface of the bone plate is provided. The through hole extends from the first surface through the bone plate to the second surface, wherein the contact surface is formed by at least part of the inner surface. The deformable contact region comprises a plurality of cavities at least partially surrounding the through hole and each substantially extending in a height direction of the bone plate.

The height direction may substantially correspond to the direction of the through hole axis, or may be tilted with respect to the through hole axis. Further, the height direction may be substantially perpendicular to the first and second surfaces of the bone plate, or may be tilted with respect to the first and second surfaces.

The shape of the bone plate may be adapted to the geometry of the bone to be supported. For example, the bone plate may be a flat plate of a parallelepiped shape, or it may be a plate with an uneven (e.g., curved) surface of an arbitrary shape.

The one or more through holes may be provided for inserting a fastening member such as a bone screw. The fastening member may be configured for entering the bone, thereby fixing the bone plate with respect to the bone.

At least one of the through holes may be configured such that it has a cross-sectional dimension that is smaller than a maximum cross-sectional dimension of the fastening member, so that the fastening member contacts the bone plate at its inner surface when being inserted into the through hole. The maximum cross-sectional dimension of the fastening member is usually defined by the head of the fastening member. In the case of a screw, the screw head may thus have a greater cross-sectional dimension than the screw shaft adjoining the screw head. Accordingly, when a fastening member is inserted into the through hole, a gap between the fastening member and the bone plate is closed as the head of the fastening member enters the through hole.

The through hole may have different shapes. For example, the through hole may be formed by countersinks that extend from the first and second surfaces of the bone plate into the inside of the bone plate (thereby defining, e.g., conical or spherical inner surface portions with a diameter increasing from the respective first and second surfaces towards the centre of the bone plate in a height direction of the bone plate). The through hole may also be a hole with a constant diameter defining a cylindrical inner surface or inner surface portion. In another variant, the through hole may be formed by only one countersink extending from the first or second surface into the inside of the bone plate, or it may define a curved inner surface with a continuously increasing diameter.

The deformable contact region comprises a plurality of cavities that at least partially surround the through hole and substantially extend in a height direction of the bone plate. The plurality of cavities may be arranged so as to completely surround the through hole, with a fixed distance between adjacent cavities or with varying distances between adjacent cavities in a circumferential direction of the through hole. In an implementation with varying distances between adjacent cavities, the plurality of cavities may be arranged so as to form one pattern or a plurality of patterns with each pattern comprising a plurality of cavities, wherein between two adjacent patterns of a plurality of patterns no cavities are provided. In this way, the plurality of cavities may be concentrated at specific regions around the through hole, thereby only partially surrounding the through hole. If, for example, the plurality of cavities are formed so as to be adjacent to only one side of the through hole, a polyaxiality may be provided in a specific direction, e.g. a biased direction.

By providing the bone plate with the cavities, an anisotropic material structure may be created. As such, the extent of deformation may depend on the direction of the load acting upon the material structure. In the present case, the material structure may have a relatively low stiffness in a cross-sectional direction of the cavities (e.g., in a direction that is substantially orthogonal to the height direction) and a relatively high stiffness in the height direction.

When a fastening member is inserted into a through hole that is at least partially surrounded by the anisotropic material structure, the relative softness of the material structure in a cross-sectional direction of the cavities may allow the fastening member to be inserted with low effort and at the same time allow a reliable locking. For example, when a (e.g., threaded) head of the fastening member enters the through hole and contacts the inner surface of the through hole, the bone plate starts to be deformed and to adapt its shape to the outer shape of the head of the fastening member. In this way, the bone plate can lock with the head of the fastening member at a certain angular relationship.

In one implementation, a length of at least some of the cavities in the height direction is at least ten (e.g., fifteen or twenty) times greater than a cross-sectional dimension of the at least some cavities in a direction lying in a plane perpendicular to the height direction. Cavities with such high aspect ratios may be for example manufactured by means of a laser drilling process or 3D printing.

The plurality of cavities may form a pattern extending radially outwards from the axis of the through hole. The plurality of cavities forming the pattern may have substantially the same cross-sectional dimension in a direction extending radially outwards from the through hole axis, or the plurality of cavities may for example be configured such that the cross-sectional dimension of a cavity decreases with an increasing distance from the through hole axis. By varying the cross-sectional dimension of the single cavities, regions with different degrees of stiffness may be created. Another or an additional possibility for creating regions with different degrees of stiffness may be created by varying the distances between adjacent cavities.

The plurality of cavities may be one of circular, hexagonal, quadrangular, and triangular in cross-section. The plurality of cavities may form at least one of through holes and blind holes in the bone plate.

In a further implementation, the contact region is configured so as to define a minimum cross-sectional dimension of the through hole. As described above, the through hole may have different configurations. As an example, it may be cylindrically shaped, with a constant diameter, but it also may have a shape with varying diameter. In this case, the contact surface may comprise that part of the inner surface where the through hole has a minimum cross-sectional dimension.

A possible implementation with varying diameter of the through hole is for example a configuration in which the contact region is formed between an upper region of the bone plate comprising the first surface and a lower region of the bone plate comprising the second surface. In the respective upper and lower regions the through hole may then be formed with an increasing cross-sectional dimension in a direction from the contact region to the respective first and second surfaces.

According to a second aspect, a bone plate is provided which comprises a first surface and a second surface opposite to the first surface, a deformable contact region comprising a contact surface, and a through hole defining a through hole axis and an inner surface of the bone plate and extending from the first surface through the bone plate to the second surface. The contact surface is formed by at least part of the inner surface, wherein the deformable contact region comprises at least one cavity surrounding the through hole in a circumferential direction of the through hole.

Also in the second aspect an anisotropic material structure may be created, with, for example, a relative low stiffness in a radial direction of the cavity compared to an orthogonal direction thereto (e.g., in a height direction of the bone plate). A fastening member may thus be allowed to be inserted into the through hole such that, when the fastening member continues to enter the through hole, the cavity is deformed so to adapt its shape to the outer shape of the fastening member, thereby locking the fastening member with the bone plate. As in the first aspect, the above described locking may substantially be independent from the insertion angle with which the fastening member is inserted into the through hole, so that the fastening member can be locked with the bone plate in any desired angular relationship.

The bone plate may further comprise at least one wall enclosing the at least one cavity, wherein at least part of the at least one wall facing the through hole defines the contact surface. In this configuration, when a fastening member is inserted into the through hole, the wall enclosing the cavity can be deformed so as to adapt its shape to the outer shape of the fastening member, thereby locking the fastening member with the bone plate. The at least one wall enclosing the cavity may for example be circular in cross section.

The contact region may in the second aspect be configured so as to define a minimum cross-sectional dimension of the through hole. As described above in connection with the first aspect, the through hole may have different configurations. It may be cylindrically shaped, with a constant diameter, but it also may have a shape with varying diameter. The contact surface may comprise that part of the inner surface where the through hole has a minimum cross-sectional dimension.

A possible implementation with varying diameter of the through hole is for example a configuration in which the contact region is formed between an upper region of the bone plate comprising the first surface and a lower region of the bone plate comprising the second surface. In the respective upper and lower regions the through hole may then be formed with an increasing cross-sectional dimension in a direction from the contact region to the respective first and second surfaces.

The cavity or cavities may be formed in the bone plate itself, or, alternatively, the bone plate may comprise an insert fitted to a wall of the bone plate so as to form or close the cavity or cavities. As an example, the at least one cavity may be formed in the insert which is fitted to a wall of the bone plate.

The contact region may comprise exactly one cavity surrounding the through hole, but it may also comprise a sequence of two or more cavities surrounding the through hole. Further, the contact region may also comprise a plurality of cavities, each at least partly surrounding the through hole in a circumferential direction thereof, wherein the plurality of cavities form a pattern that extends in a height direction of the bone plate and/or extends radially outwards from the through hole axis. A possible process for forming the cavity or cavities is a 3D printing process. The cavities may encircle the inner surface of the through hole in a multiplicity of axially spaced rows with the cavities open to the inner surface.

A further possible implementation is a bone plate with a contact region that comprises cavities according to both the first aspect and the second aspect. Accordingly, a bone plate may be provided that comprises a contact region with a plurality of cavities that at least partially surround the through hole and extend in a height direction of the bone plate, and, in addition, one or a plurality of further cavities surrounding the through hole in a circumferential direction of the through hole. The further cavities surrounding the through hole in a circumferential direction thereof may form a pattern that extends in a height direction of the bone plate and/or extends radially outwards from the through hole axis.

Further provided is a bone plate system which comprises a bone plate as presented herein (e.g., in accordance with any of the first and second aspect presented above), and which further comprises a fastening member which is configured to cooperate with the deformable contact region of the bone plate. The fastening member comprises an at least partially threaded elongated section and a threaded head section adjoining the elongated section disposed along a fastening member axis. The threaded head section and the contact region are configured such that a rigid fixation of the fastening means to the bone plate is allowed at a plurality of insertion angles defined between the fastener member axis and the through hole axis.

The threaded head section of the fastening member and the deformable contact region of the bone plate may for example be configured such that, upon cooperation of the threaded head section with the deformable contact region, the deformable contact region is deformed so as to lock with the threaded head section in a certain angular relationship. The deformable contact region may be a (e.g., tappable) contact region deformed by the threaded head section so as to adapt its shape to the shape of the threaded head section. The threaded head section may thus cut a thread in the contact region upon inserting the fastening member into bone.

The threaded head section of the fastening member may have various shapes. It may for example have one of a conical and spherical outer shape.

BRIEF DESCRIPTION OF THE DRAWINGS

Further aspects, details and advantages of the present disclosure will become apparent from the following description of exemplary embodiments in conjunction with accompanying drawings, wherein:

FIG. 9 schematically illustrates in a perspective view an embodiment of the second variant of an anisotropic structure of the bone plate forming the deformable contact region.

DETAILED DESCRIPTION

In the following description of exemplary embodiments, for purposes of explanation and not limitation, specific details are set forth, such as particular configurations of the deformable contact region, in order to provide a thorough understanding of the disclosure presented herein. It will be apparent to one skilled in the art that this disclosure may be practiced in other embodiments that depart from these specific details, for example in size, arrangement and cross-sectional configuration of the cavity or cavities. Also, the shape (e.g., outer contour and/or curvature) of the bone plate may be adapted to the anatomical needs.

Figure 1:
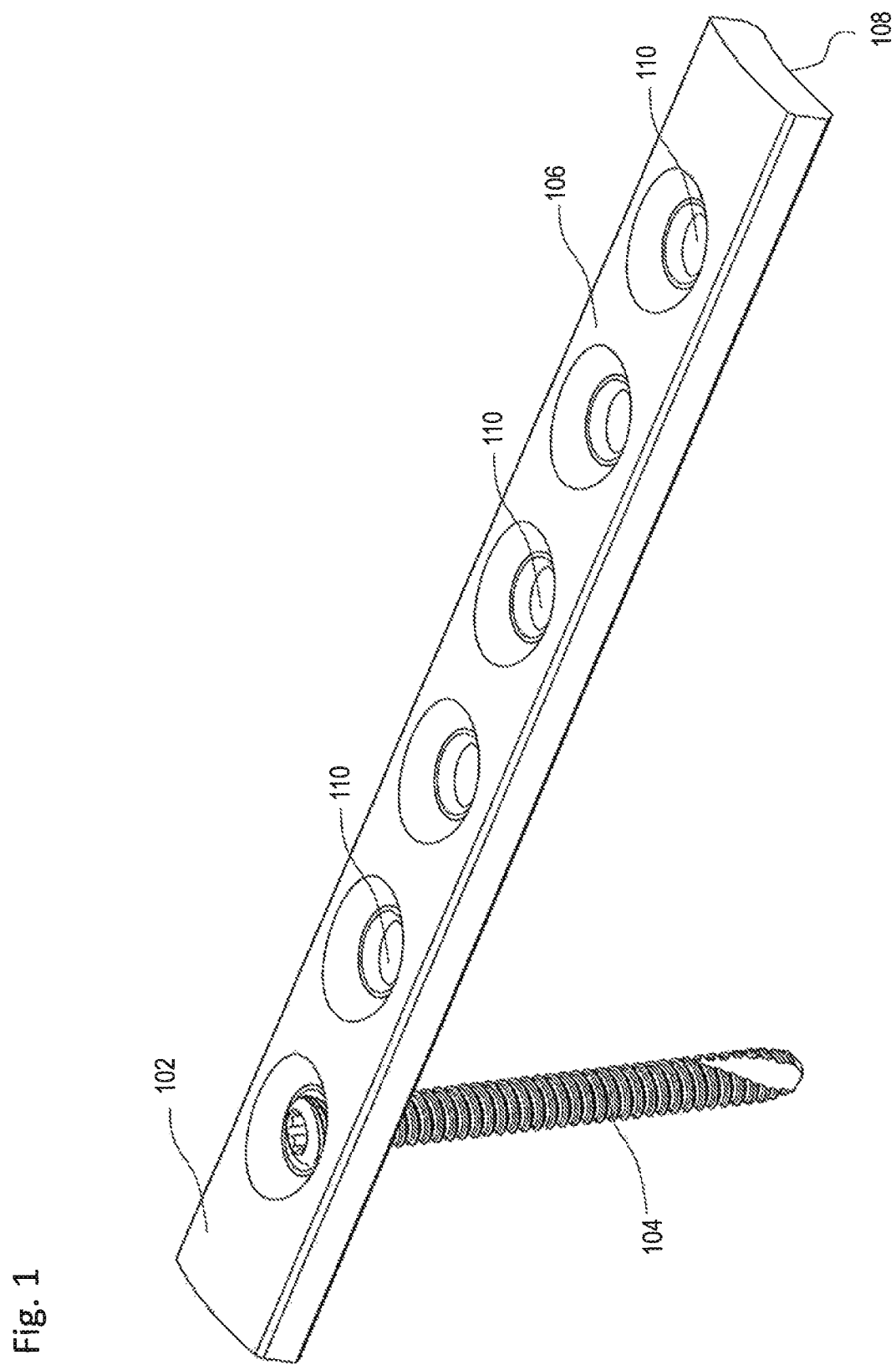
FIG. 1 schematically illustrates an embodiment of a bone plate system comprising a bone plate with through holes for cooperating with corresponding fastening members.

FIG. 1 illustrates an embodiment of a bone plate system which comprises a bone plate 102 and at least one fastening member 104.

The bone plate 102 has a first surface 106 and a second surface 108 which is arranged opposite to the first surface 106. The bone plate 102 further comprises a plurality of through holes 110 that, in the present embodiment, are arranged in a longitudinal direction of the bone plate 102 and which extend from the first surface 106 to the second surface 108 through the bone plate 102 in a height direction of the bone plate 102.

The fastening member 104 is shown to be inserted into one of the through holes 110 at a desired insertion angle (i.e., a desired angle with respect to a central through hole axis). In the present embodiment, the fastening member 104 is a screw and is inserted into the through hole 110 with an insertion angle that is different from zero, so that the fastening member 104 is tilted with respect to the through hole axis.

Figure 2:
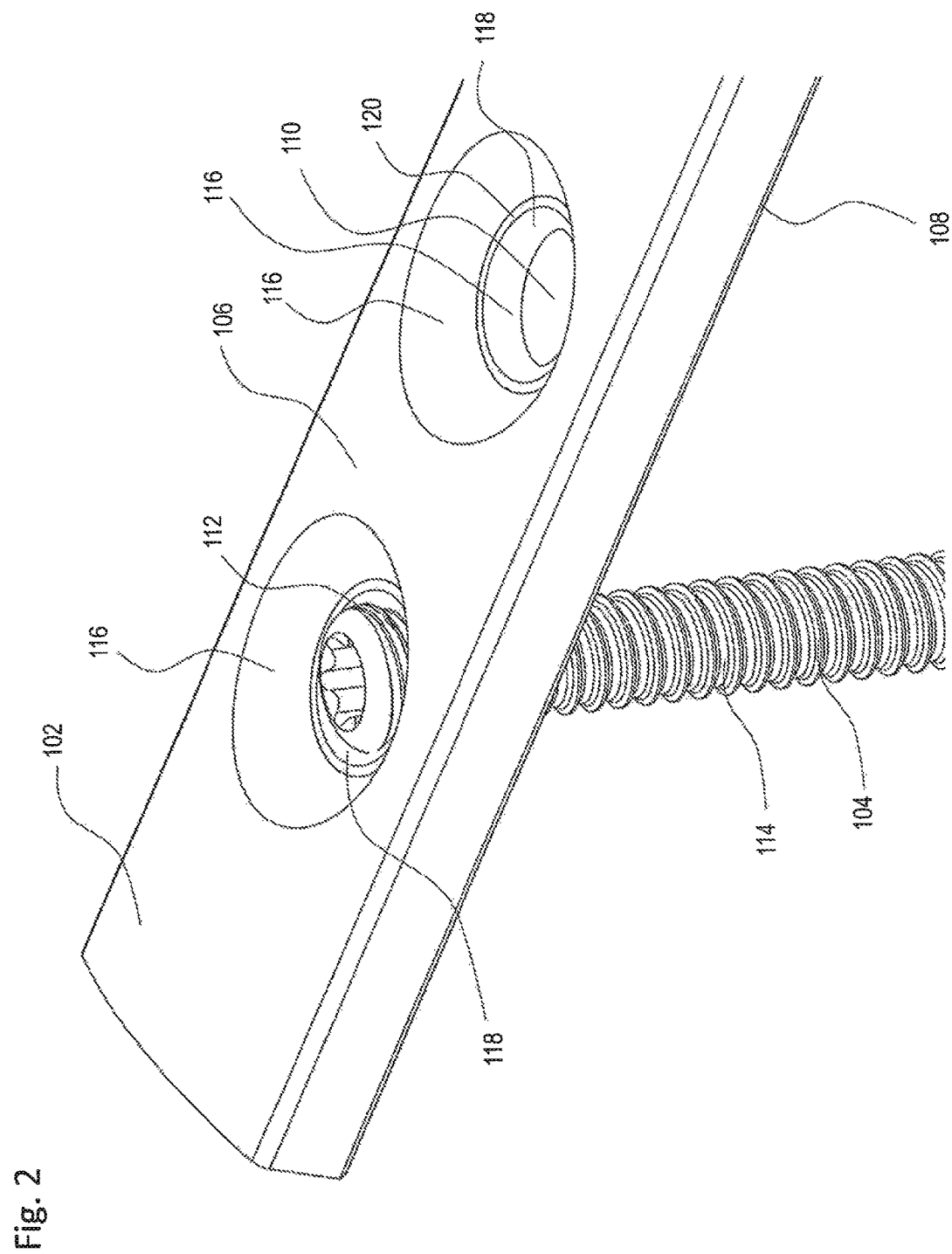
FIG. 2 is a detailed view of the bone plate system of FIG. 1.

In FIG. 2, the screw 104 of FIG. 1 inserted into the bone plate 102 of FIG. 1 is shown in a detailed view. As can be seen, the fastening member 104 comprises a threaded head section 112 and a threaded elongated section 114 adjoining the threaded head section 112 and both extending along a longitudinal screw axis. As can be further seen, the through hole 110 defines an inner surface 116 of the bone plate 102, which has a partially conical shape, and which defines a contact surface 118 for cooperating with the fastening member 104. The contact surface 118 is part of a contact region 120 formed in or integrated into the bone plate 102.

As will be later described in more detail, the fastening member 104 cooperates with the contact region 120 of the bone plate 102. The contact region 120 is configured such that the fastening member 104 can be rigidly fixed with respect to the bone plate 102 in a certain angular relationship while providing a sufficiently large cantilever bending resistance.

Figure 3:
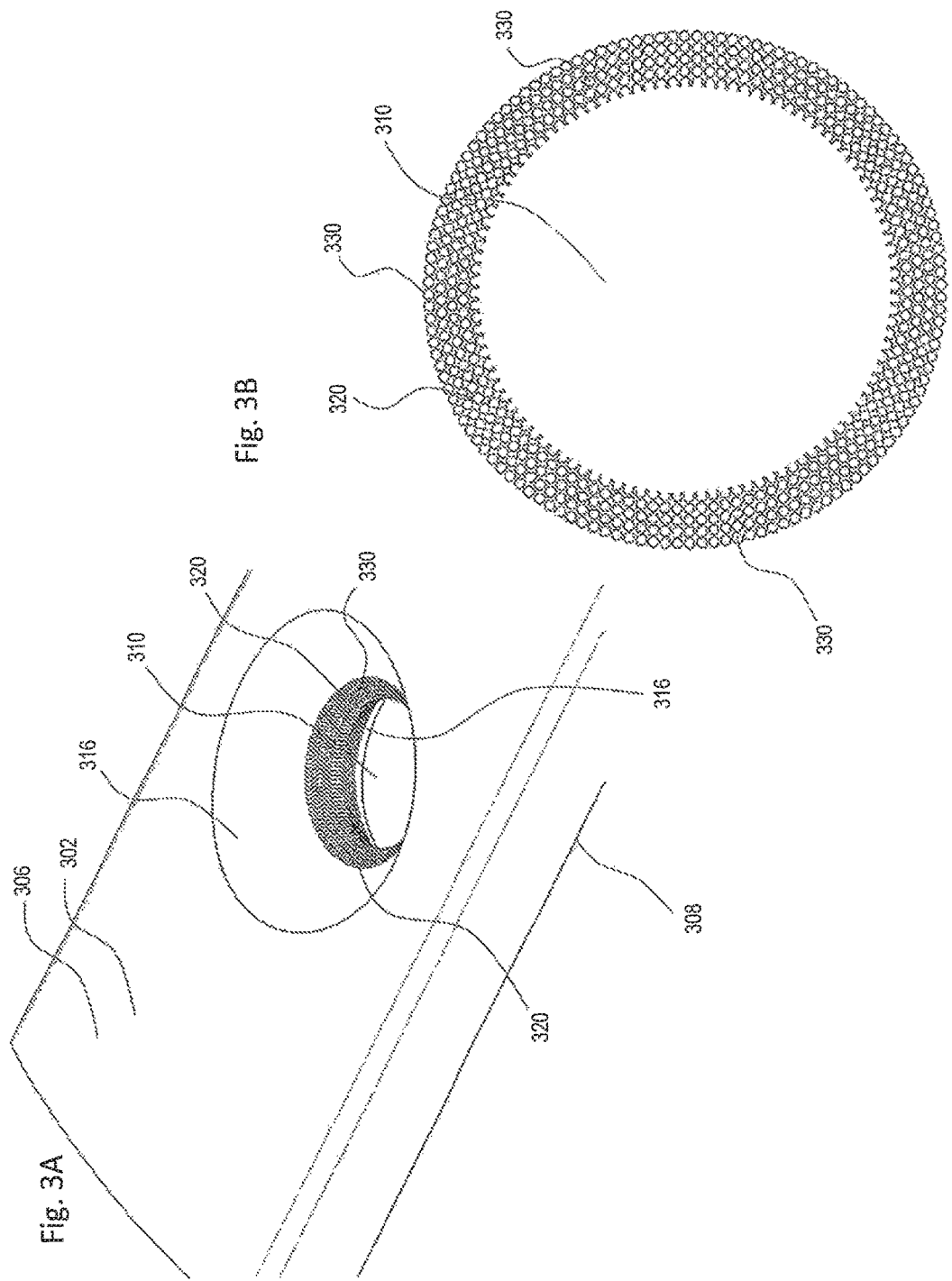
FIG. 3A, 3B schematically illustrate a first variant of an anisotropic structure of the bone plate forming the deformable contact region, in a perspective view viewed from above, and in a cross-sectional view schematically showing the region comprising a plurality of cavities extending in a height direction of the bone plate.

FIGS. 3A and 3B show a first variant of a bone plate 302 (e.g., the bone plate 102 of FIGS. 1 and 2). More specifically, FIG. 3A shows a first variant of the bone plate 302 with a through hole 310 extending in a height direction through the bone plate 302. The through hole 310 is formed by a first countersink portion extending from the first surface 306 through the bone plate 302 in an upper region of the bone plate 302 and a second countersink portion extending from the second surface through the bone plate 302 in a lower region of the bone plate 302. The so-formed through hole 310 with a diameter continuously increasing in a direction towards the first and second surfaces 306, 308 defines conical inner surfaces 316 of the bone plate 302. The region of the bone plate 302 adjoining the center part of the through hole 310 with a minimum diameter of the through hole 310 forms the contact region 320 between the bone plate 302 and a fastening member (not shown).

In the present embodiment, the contact region 320 comprises a plurality of cavities that extend in a height direction of the bone plate 302 and that form a pattern that surrounds the through hole 310. Further, the pattern is configured so as to extend radially outwards from the axis of the through hole 310. The plurality of cavities are formed as through holes 310, but alternatively it is also possible to form them as blind holes.

FIG. 3B shows the cavity pattern in a cross-sectional view parallel to the first surface 306. As can be seen, the cavities 330 each have a circular cross-section and are homogenously distributed around the through hole 310 so as to fully surround the through hole 310 with a substantially constant density in a radial direction and a circumferential direction of the through hole 310. Further, the plurality of cavities 330 in this particular embodiment substantially have the same diameter.

The plurality of cavities 330 formed around the through hole 310 with the inner diameter continuously increasing from an inner or centre part of the bone plate 302 towards the first and second surfaces 306, 308 have a greater dimension in a height direction of the bone plate 302 if they are located further away from the through hole 310, i.e., the height dimension of the cavities 330, which are here formed as through holes, increases with an increasing distance of the cavities 330 from the axis of the through hole 310 in a radial direction thereof due to the variable thickness of the bone plate 302 around the through hole 310.

At least some of the cavities 330 have a length in the height direction that is greater than the cross-sectional dimension of the at least some cavities 330 in a direction lying in a parallel plane to the first and second surfaces. That means that, in the variant shown in FIGS. 3A and 3B, the cavities 330 that are located further away from the through hole 310 in a radial direction thereof and that have a greater length in a height direction of the bone plate 302 than the cavities 330 located nearer to the through hole 310 have a length in the height direction that is greater than the diameter of the cavities 330. The length in the height direction of these cavities 330 may be at least ten times greater than the cross-sectional dimension of these cavities 330 in a direction lying in a parallel plane to the first and second surfaces 306, 308, (i.e., the diameter of the cavities). This ratio could also exceed 20, 40 or even 60 for at least some of the cavities 330.

In the variant shown in FIGS. 3A and 3B, the diameter of the cavities 330 (i.e., the cross-sectional dimension in a direction lying in a plane perpendicular to the height direction) is substantially the same for all cavities 330. In another implementation, the individual cross-sectional dimension of the cavities 330 may vary. For example, the cross-sectional dimension of a cavity 330 of the plurality of cavities 330 that form the pattern may decrease with an increasing distance from the axis of the through hole 310.

Also, in the illustrated variant, the plurality of cavities 330 are circular in cross-section. In other implementations, the plurality of cavities 330 may be differently shaped (e.g., they may be hexagonal, quadrangular or triangular in cross-section).

Furthermore, in the variant shown in FIGS. 3A and 3B, the plurality of cavities 330 extend in a direction that is substantially perpendicular to the first and second surfaces 306, 308 of the bone plate 302 and that is substantially parallel to the through hole axis. Alternatively, the plurality of cavities 330 may also extend in a direction that is not perpendicular to the first and second surfaces of the bone plate and/or not parallel to the through hole axis (e.g., at an angle of up to 20° or up to 45°).

In the variant shown in FIGS. 3A and 3B, the cavities 330 are homogenously distributed in a circumferential direction of the through hole 310 and in a radial direction thereof. As such, they are formed with a constant density in the contact region 320. In other implementations, the density of the cavities 330 may vary in the contact region 320. For example, the density of the cavities 330 may vary in the radial direction, for example so as to decrease with an increasing distance from the through hole 310 in a radial direction thereof. Alternatively or in addition, the density of the cavities 330 may also vary in a circumferential direction of the through hole 310. For example, the cavities 330 may form a plurality of patterns that are locally concentrated at specific positions adjacent to the through hole 310, so that the cavities 330 only partially surround the through hole 310.

The plurality of cavities 330 may be formed by a laser drilling process. Laser drilling processes are advantageous in forming high aspect ratio holes and present fast and accurate processes for forming holes.

The plurality of cavities 330 may be formed in the bone plate 302 itself. Alternatively, the bone plate 302 may comprise an insert that comprises the plurality of cavities 330 and which is subsequently fitted to a wall of the bone plate 302. At least part of the contact surface 316 is then formed by an outer wall of the insert. The insert may be formed by 3D printing (and, optionally, laser drilling) or in any other way.

Figure 4:
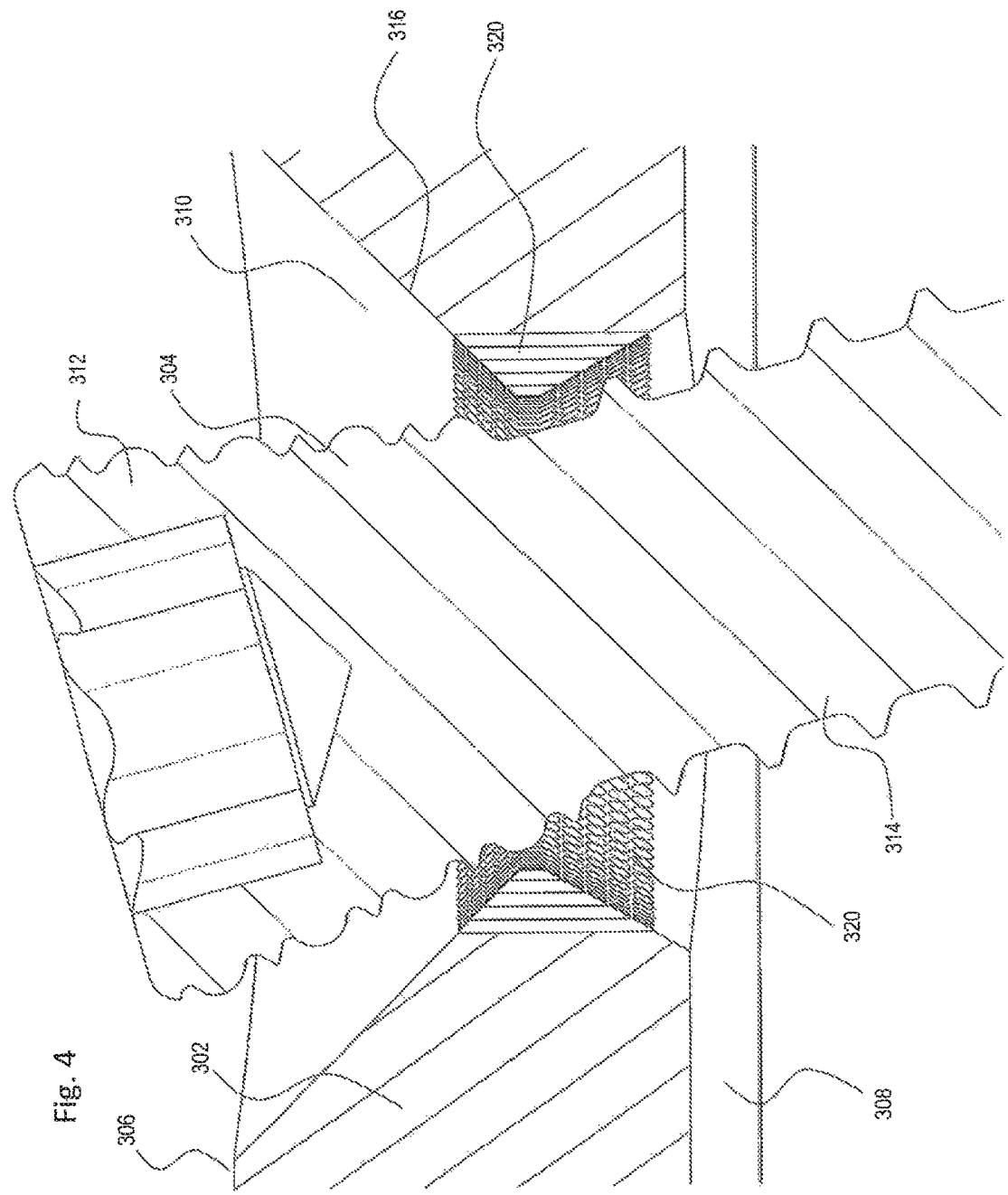
FIG. 4 schematically illustrates a fastening member cooperating with a bone plate as illustrated in FIGS. 3A, 3B, in a state where the fastening member is only partially inserted into the through hole with a desired insertion angle.
Figure 5:
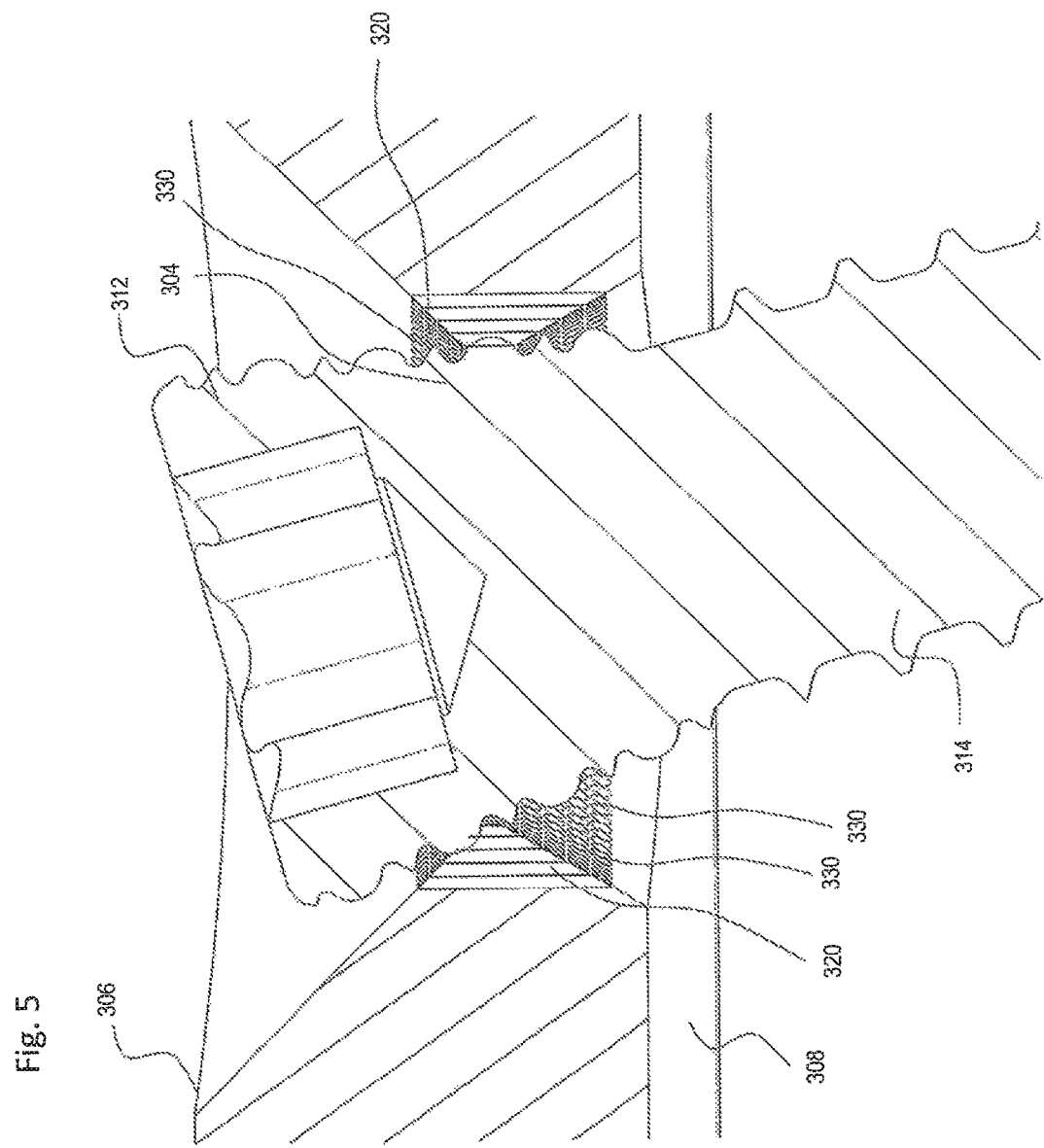
FIG. 5 schematically illustrates the fastening member of FIG. 4 cooperating with the bone plate as illustrated in FIGS. 3A, 3B, in a state where the fastening member is further inserted into the through hole shown in FIG. 4, but not fully inserted.
Figure 6:
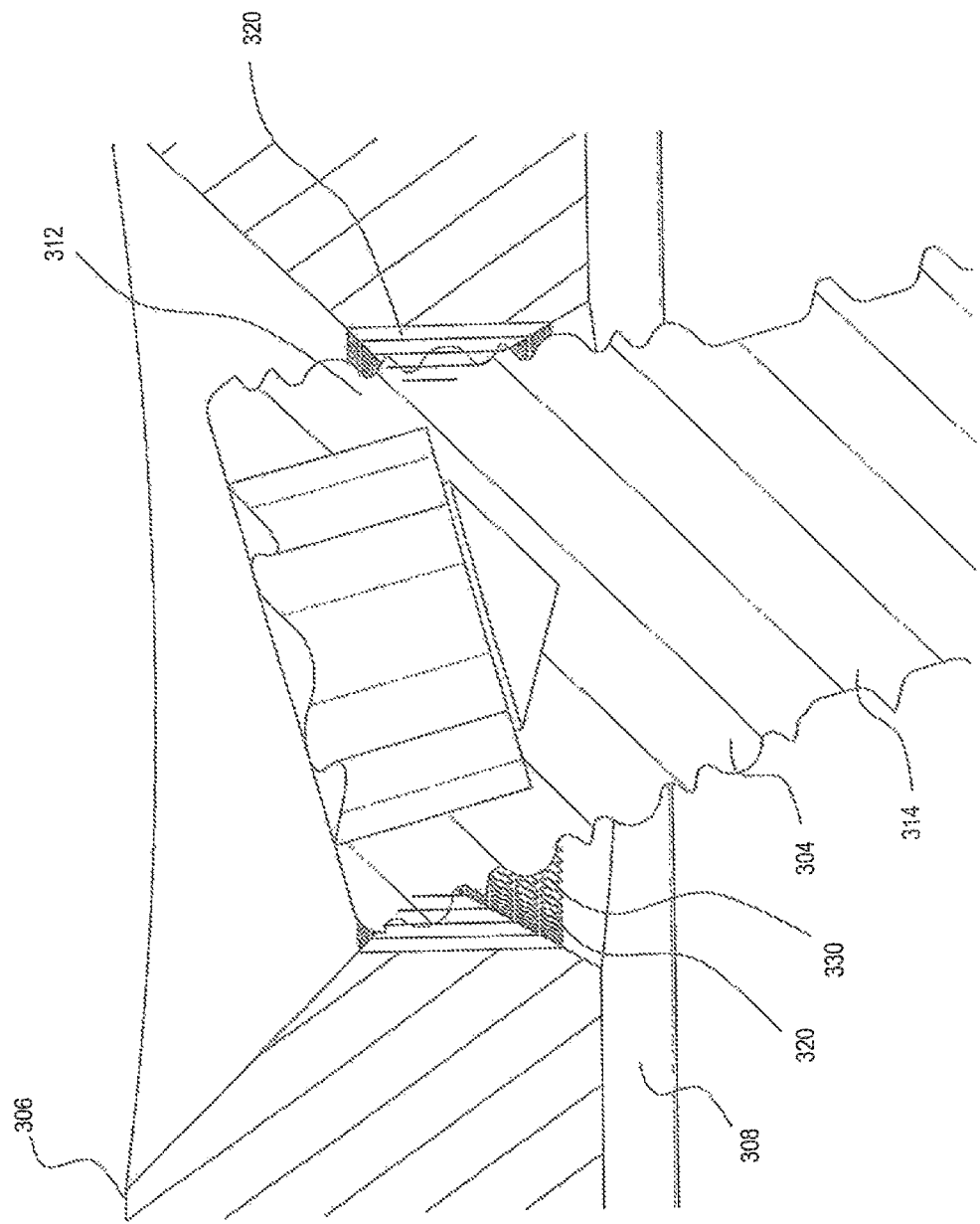
FIG. 6 schematically illustrates the fastening member of FIG. 4 and FIG. 5 cooperating with the bone plate as illustrated in FIGS. 3A, 3B, in a state where the fastening member is fully inserted into the through hole.

In FIGS. 4 to 6, it is illustrated how a fastening member in the form of a screw 304 is inserted into one of the through holes 310 of the bone plate 302 and how the screw 304 interacts with the contact region 320 formed in the bone plate 302. As described above, the screw 304 has a conically shaped threaded head section 312 and a threaded elongate section 314. In other implementations, the fastening member 304 may be differently shaped, for example with a head section 314 having a constant cross-sectional dimension.

In FIG. 4, the screw 304 is shown to be partially inserted into the through hole 310 at a definite insertion angle with respect to the through hole axis, wherein in the illustrated arrangement the definite insertion angle is different from zero. The through hole axis is an axis going through the centre of the through hole. In the state shown in FIG. 4, the diameter of the screw 304 of the part of the screw 304 that is located in the vicinity to the contact region 320 of the bone plate 302 is smaller than the minimum diameter of the through hole 310 defined by the contact region 320, so that the screw 304 does not contact the contact region 320. Therefore, the contact region 320 is not (yet) deformed by the screw 304.

In FIG. 5, the screw 304 is shown to be further inserted into the through hole 310 than in FIG. 4, so that the conical screw head section 312 having a larger diameter than the elongated screw section 314 gets into contact with the contact region 320. In this state, the screw 304 contacts the contact region 320 so as to cooperate with the contact region 320. In particular, the thread of rigid screw head section 312 starts to deform the contact region 320 comprising the plurality of cavities 330 extending in a height direction of the bone plate 302. As such, a complementary thread is cut in the contact region 320.

In FIG. 6, the screw 304 is shown to be fully inserted into the through hole 310. In this state, the contact region 320 is shown to be deformed so as to have a corresponding shape to that of the screw 304. As a result, the screw 304 is rigidly locked to the plate 302 in a desired angular relationship by the thread of the screw head being in firm engagement with the complementary thread that has been cut in the contact region 320.

Figure 7:
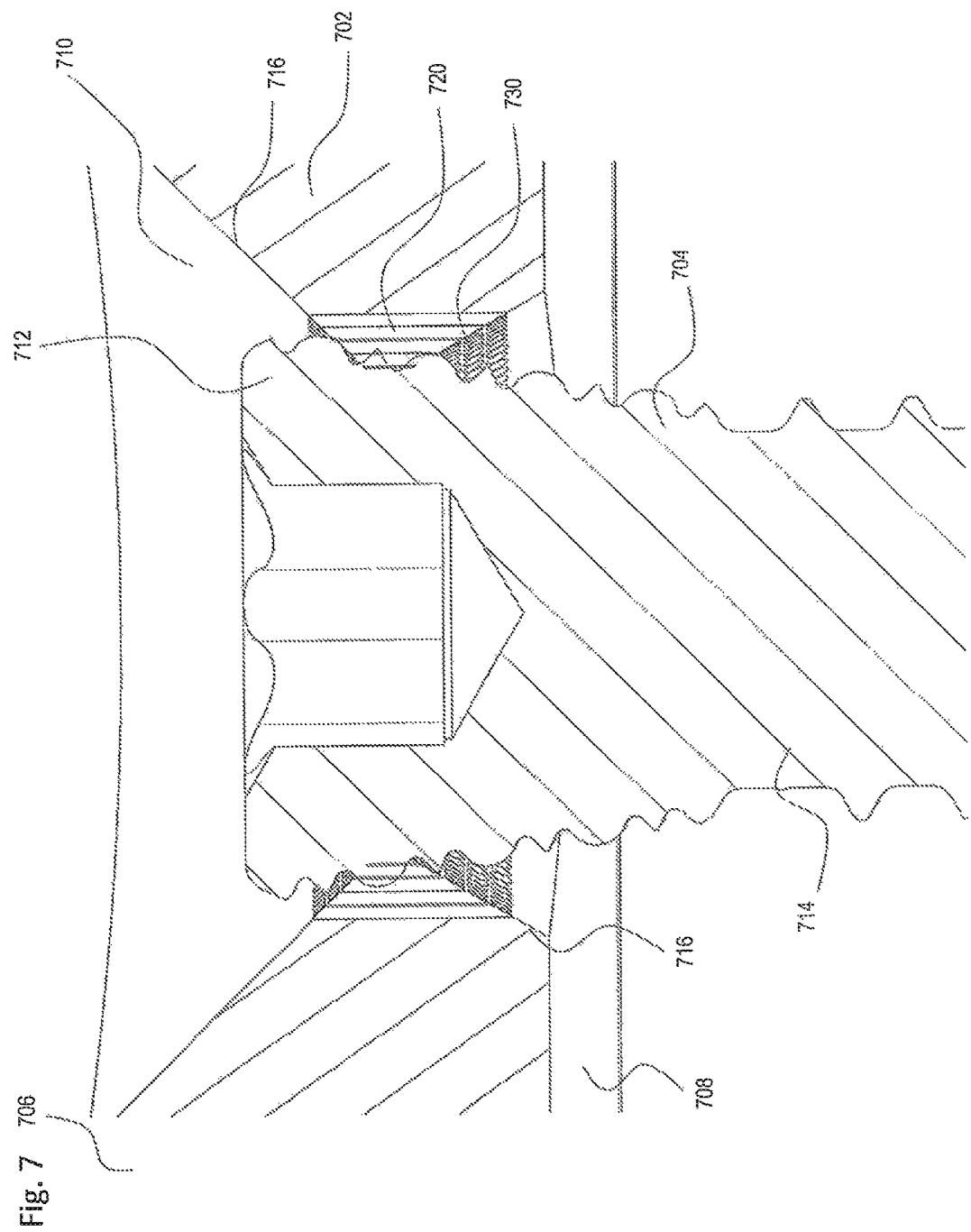
FIG. 7 schematically illustrates a fastening member being inserted into a through hole of a bone plate as illustrated in FIGS. 3A, 3B, with another insertion angle than the fastening member of FIGS. 4 to 6.

In FIG. 7, a screw 704 is shown to be inserted into one of the through holes 710 of the bone plate 702, wherein the insertion angle between the screw 704 and the bone plate 702 is approximately zero (i.e., the screw axis is substantially parallel to the through hole axis and substantially perpendicular to the first and second surfaces 706, 708 of the bone plate 702). As can be derived from FIG. 7, also in this arrangement, the screw 704, upon contacting the inner surface 716 of the through hole 710, deforms the material of the bone plate 702 so that the contact region 720 locks with the threaded screw head section 712 in the desired angular relationship.

The plurality of cavities 330, 730 provided in the bone plate 302, 702 provide an anisotropic material structure in the bone plate 302, 702. This means that the strength of the material depends on the direction in the material. More specifically, the disclosed structure with the plurality of cavities 330, 730 extending in a height direction of the bone plate 302, 702 in the vicinity of the through hole 310, 710 have the effect that the bone plate 302, 702 has a higher material strength in a direction parallel to the height direction along which the cavities 330, 730 extend, which is in the variant shown in FIGS. 3 to 7 a direction parallel to the through hole axis, than in a direction orthogonal to that direction (i.e., in a radial direction). Thus, a structure around the through hole 310, 710 is provided that is relatively stiff in the axial direction and relatively soft in a radial direction.

Consequently, when the screw 304, 704 is inserted into the through hole 310, 710 so that the screw head section 312, 712 contacts the bone plate 302, 702, the relative softness in a radial direction allows the screw 304, 704 to be inserted further with low effort, since the bone plate 302, 702 can be easily deformed in the radial direction. Thus, when the screw head section 312, 712 continues to enter the through hole 310, 710, a gap existing between the screw 304, 704 and the bone plate 302, 702 is closed due to the larger cross-sectional dimension of the screw head section 312, 712 than that of the screw shaft section 314, 714 and the radial forces exerted on the bone plate 302, 702 are increased. Further, because of the relative softness of the bone plate material in the radial direction, the bone plate 302, 702 is deformed so as adapt its shape to the outer shape (i.e., the thread) of the screw head section 312, 712 thereby locking the screw head section 312, 712 with the bone plate 302, 702.

The above described locking between the head section 312, 712 and the bone plate 302, 702 is substantially independent from the insertion angle with which the screw 304, 704 is inserted into the through hole 310, 710, so that the fastening member 304, 704 can be locked with the bone plate 302, 702 in any desired angular relationship.

When a bending load is applied to the screw elongated section 314, 714 (i.e., a force that is directed orthogonal to the screw axis), shear forces act upon the bone plate 302, 702 in directions substantially parallel to the through hole axis. Due to the high stiffness of the bone plate material in the contact region 320, 720 of the bone plate 302, 702 in a direction parallel to the through hole axis, the bone plate 302, 702 provides a good resistance again deformation when the fastening member 304, 704 is exposed to bending forces.

Figure 8:
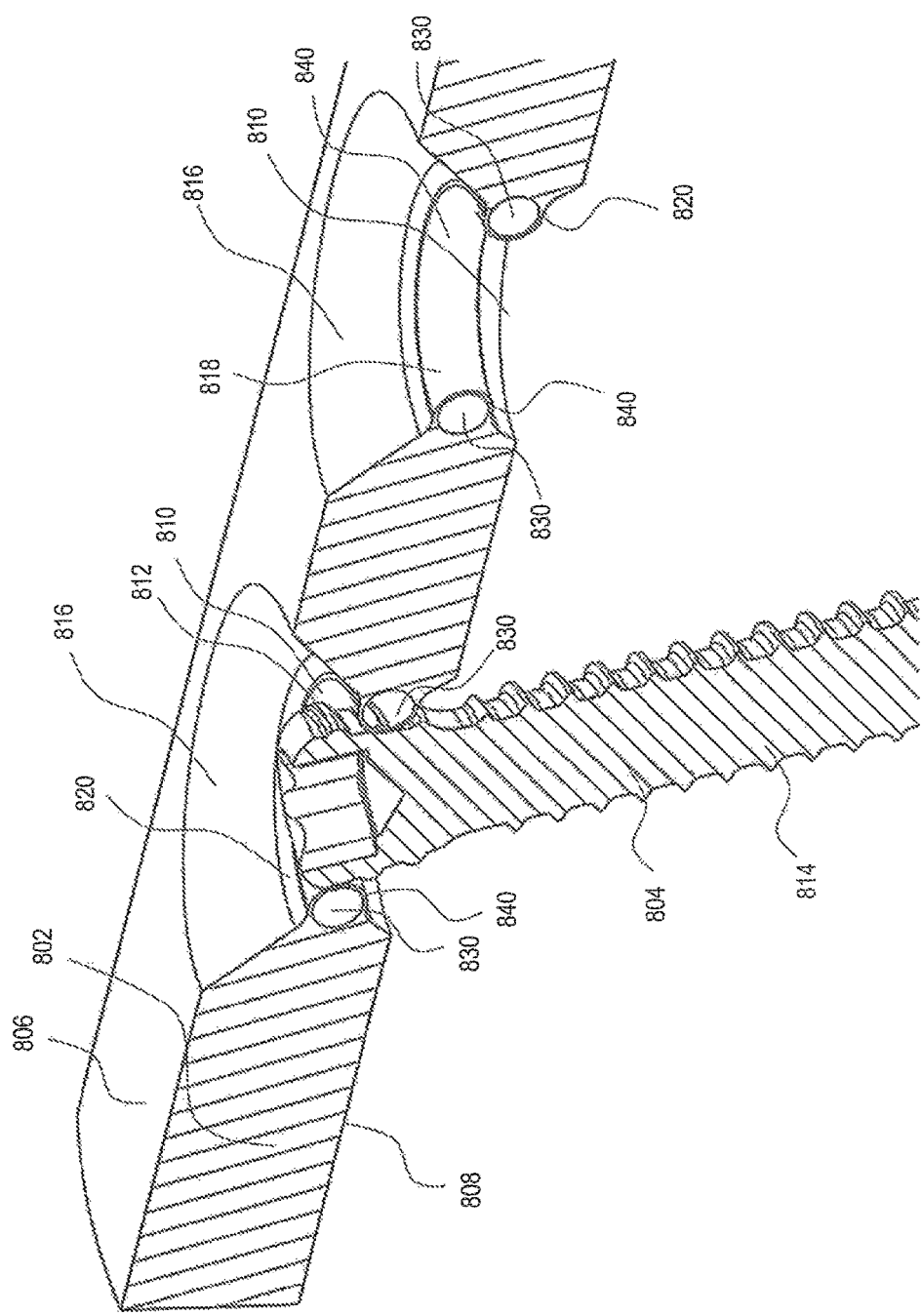
FIG. 8 schematically illustrates in a perspective view a second variant of an anisotropic structure of the bone plate forming the deformable contact region, with a fastening member being fully inserted into the through hole with a desired insertion angle.

FIG. 8 illustrates a second variant of a bone plate 802 (e.g., the bone plate 102 of FIGS. 1 and 2). Similar to the first variant shown in FIGS. 3 to 7, the bone plate 802 of the second variant comprises a first surface 806 and a second surface 808 located opposite to the first surface 806, and one or more through holes 810 defining respective through hole axes are formed in the bone plate 802, which extend from the first surface 806 to the second surface 808 through the bone plate 802. The through holes 810 define inner surfaces 816 of the bone plate 802. Further, similar to the first variant, the through hole 810 is formed by a first countersink portion extending from the first surface 806 through the bone plate 802 in an upper region of the bone plate 802 and a second countersink portion extending from the second surface 808 through the bone plate 802 in a lower region of the bone plate 802. The region of the bone plate 802 adjoining the center part of the through hole 810 with a minimum diameter of the through hole 810 (i.e., the region between the upper and lower diverging regions) forms the contact region 820 between the bone plate 802 and the fastening member 804.

As can be seen in FIG. 8, other than in the first variant of FIGS. 3 to 7, the deformable contact region 820 comprises a cavity 830 extending in a circumferential direction of the through hole 810. The cavity 830 is enclosed by a wall 840, wherein the part of the wall 840 that faces the through hole 810 defines the contact surface 818 between the fastening member 804 and the bone plate 802.

In the illustrated implementation, one cavity 830 is shown to surround the through hole 810 in a circumferential direction thereof, and one wall 840 is enclosing the cavity 830, which is circular in cross-section. However, in other implementations, the through hole 810 may be circumferentially surrounded by a sequence of two or more cavities 830, which are each enclosed by a wall 840 which may also separate the cavities 830 from each other. Moreover, the cavity or the cavities 830 may be differently shaped, for example elliptical in cross-section.

Furthermore, in still another implementation of the second variant, which is shown in FIG. 9 of the drawings, the bone plate 902 comprises one or more through holes 910 which is or are surrounded by a plurality of cavities 930 each surrounding the through hole 910 in a circumferential direction thereby forming a pattern. The plurality of cavities 930 surrounding one through hole 910 are formed so that the pattern extends in the height direction of the bone plate 902, and so that the pattern extends radially outwards from the through hole axis. In the implementation shown in FIG. 9, the plurality of cavities 930 are inhomogeneously distributed around the through hole 910, both in the height direction of the bone plate 902 and in the radial direction thereof. Alternatively, it is also possible to homogeneously distribute the plurality of cavities 930 around the through hole 910, in the height direction and in the radial direction, or in only one direction thereof.

The cavity or cavities 830 may be formed in the bone plate 802, 902 itself, or (at least partially) in an insert which is fitted to the bone plate 802, 902. As an example, the cavity or cavities 830, 930 may be formed by a three dimensional (3D) printing process.

In FIG. 8, a fastening member 804, which in the present case is a screw with a threaded head section 812 of conical shape and a threaded elongate section 814, is shown to be inserted into one of the through holes 810. Like in the first variant, the threaded head section 812 contacts the contact surface 818 of the contact region 820 of the bone plate 802, which is in the illustrated second variant formed by part of the wall 840 enclosing the cavity 830. Due to the thinness of the wall 840 between the screw head section 812 and the cavity 830 resulting in a relative softness in a radial direction of the cavity 830 compared to an orthogonal direction thereto, the screw 804 is allowed to be inserted with a relative low effort. Thus, when the screw head section 812 continues to enter the through hole 810, the wall 840 enclosing the cavity 830 is deformed so as adapt its shape to the outer shape of the threaded screw head section 812 thereby locking the screw head section 812 with the bone plate 802.

As in the first variant, the above described locking between the head section 812 and the bone plate 802 is substantially independent from the insertion angle with which the screw 802 is inserted into the through hole 810, so that the fastening member 804 can be locked with the bone plate 802 in a wide range of angular relationships.

When a bending load is applied to the screw shaft section 814 (i.e., a force that is directed orthogonal to the screw axis) shear forces act upon the bone plate 802 in directions parallel to the through hole axis, (i.e., in directions orthogonal to the radial direction of the cavity 830). Due to the high stiffness of the contact region 820 formed by the cavity or cavities 830 in these directions, the bone plate 802 provides a good resistance again deformation when the fastening member 804 is exposed to bending forces.

In the present embodiments, the respective bone plate 102, 302, 702, 802, 902 has the shape of a parallelepiped, but it also may have any different shape. The plate shape usually depends on the type of bone that is fractured and on the fracture itself.

As has become apparent from the above description, the bone plates 302, 702, 802, 902 according to the first and second variants provide a polyaxial locking mechanism. The screw 304, 704, 804 is able to lock with the bone plate 302, 702, 802, 902 at a wide range of insertion angles, while offering a sufficiently high cantilever bending resistance. Thus, a surgeon using a bone plate 302, 702, 802, 902 according to the first or second variant may freely choose the screw insertion angle depending on the geometry of the fractured bone for providing a structural support to the fractured bone.

In the foregoing, embodiments and variations of the embodiments have exemplarily been described. The present invention should not be construed as being limited to the particular embodiments and their variations as discussed herein. Rather, it will be appreciated that various changes and modifications may be made by a person skilled in the art without departing from the scope of the present invention as defined in the claims that follow.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. A bone plate comprising:
a first surface and a second surface opposite to the first surface;
a deformable contact region comprising a contact surface; and
a through hole defining a through hole axis and an inner surface of the bone plate and extending from the first surface through the bone plate to the second surface,
wherein the contact surface is formed by at least part of the inner surface,
wherein the deformable contact region comprises a plurality of cavities at least partially surrounding the through hole and each substantially extending in a height direction of the bone plate, and
wherein at least one cavity of the plurality of the cavities is spaced radially from another cavity of the plurality of cavities in a direction away from the through hole axis of the bone plate.
2. The bone plate of claim 1, wherein a length of at least some of the cavities in the height direction is at least ten times greater than a cross-sectional dimension of the at least some cavities in a direction lying in a perpendicular plane to the height direction.
3. The bone plate of claim 1, wherein the plurality of cavities form a pattern extending radially outwards from the through hole axis.
4. The bone plate of claim 3, wherein a cross-sectional dimension of a cavity of the plurality of cavities forming the pattern decreases with an increasing distance from the through hole axis.
5. The bone plate of claim 1, wherein the height direction in which the plurality of cavities extend is substantially perpendicular to the first and second surfaces of the bone plate.
6. The bone plate of claim 1, wherein the plurality of cavities are one of circular, hexagonal, quadrangular, and triangular in cross-section.
7. The bone plate of claim 1, wherein the plurality of cavities are formed by a laser drilling process or by a 3D printing process.
8. The bone plate of claim 1, wherein the plurality of cavities form at least one of through holes and blind holes in the bone plate.
9. The bone plate of claim 1, wherein the contact region is configured so as to define a minimum cross-sectional dimension of the through hole.
10. The bone plate of claim 9, wherein the contact region is formed between an upper region of the bone plate comprising the first surface and a lower region of the bone plate comprising the second surface, wherein, in at least one of the respective upper and lower regions the through hole is formed with an increasing cross-sectional dimension in a direction from the contact region to the respective first and second surfaces.
11. The bone plate of claim 1, wherein the contact region comprises one or a plurality of further cavities surrounding the through hole in a circumferential direction of the through hole.
12. A bone plate system, comprising:
a bone plate according to claim 1; and
a fastening member configured to cooperate with the deformable contact region of the bone plate, wherein the fastening member comprises an at least partially threaded elongated section and a threaded head section adjoining the elongated section disposed along a fastening member axis, and wherein the threaded head section and the contact region are configured such that a rigid fixation of the fastening member to the bone plate is allowed at one of a plurality of insertion angles defined between the fastener member axis and the through hole axis.

13. The bone plate system of claim 12, wherein the threaded head section of the fastening member and the deformable contact region of the bone plate are configured such that, upon cooperation of the threaded head section with the deformable contact region, the deformable contact region is deformed so as to lock with the threaded head section in a certain angular relationship.

14. The bone plate system of claim 12, wherein a minimum cross-sectional dimension of the through hole defined by the contact region of the bone plate is smaller than a maximum cross-sectional dimension of the threaded head section of the fastening member.

15. The bone plate system of claim 12, wherein the threaded head section of the fastening member has one of a conical and spherical outer shape.

16. A bone plate comprising:
   a first surface and a second surface opposite to the first surface;
   a deformable contact region comprising a contact surface;
   a through hole defining a through hole axis and an inner surface of the bone plate and extending from the first surface through the bone plate to the second surface,
   wherein the contact surface is formed by at least part of the inner surface,
   wherein the deformable contact region comprises at least one cavity surrounding the through hole in a circumferential direction of the through hole,
   the bone plate further comprising at least one wall fully enclosing the at least one cavity.

17. The bone plate of claim 16, wherein at least part of the at least one wall facing the through hole defines the contact surface, and wherein the at least one wall enclosing the cavity is circular in cross section.

18. The bone plate of claim 16, wherein the contact region is configured so as to define a minimum cross-sectional dimension of the through hole, wherein the contact region is formed between an upper region of the bone plate comprising the first surface (106, 806) and a lower region of the bone plate comprising the second surface, and wherein in at least one of the respective upper and lower regions the through hole is formed with an increasing cross-sectional dimension in a direction from the contact region to the respective first and second surfaces.

19. The bone plate of claim 16, further comprising an insert fitted to a wall of the bone plate so as to form or close the at least one cavity.

20. The bone plate of claim 16, wherein the at least one cavity is formed by a 3D printing process.

21. The bone plate of claim 16, wherein the contact region comprises only one cavity.

22. The bone plate of claim 16, wherein the contact region comprises a plurality of cavities surrounding the through hole in a circumferential direction of the through hole, wherein the plurality of cavities form a pattern that extends in a height direction of the bone plate and/or extends radially outwards from the through hole axis.

23. A bone plate comprising:
   a first bone contacting surface and a second outwardly facing surface spaced from the first bone contacting surface;
   at least one opening in the plate having a central axis and having a first diameter at the second outwardly facing surface and a second diameter spaced from the first diameter towards the first bone contacting surface, the second diameter being less than the first diameter;
   an inner surface of the at least one opening intermediate the first bone contacting surface and the second outwardly facing surface having a multiplicity of cavities formed therein extending outwardly from the central axis and open to the inner surface of the at least one opening in the plate, the multiplicity of cavities extending around a circumference of the inner surface of the opening in a plurality of rows spaced in the axial direction of the at least one opening, wherein at least one cavity of the multiplicity of cavities is spaced radially from another cavity of the multiplicity of cavities in a direction away from the central axis of the bone plate.

* * * * *